United States Patent [19]

Schwarze et al.

[11] Patent Number: 5,313,954
[45] Date of Patent: May 24, 1994

[54] APPARATUS FOR SHOCKWAVE TREATMENT

[75] Inventors: Werner Schwarze, Stockach; Joachim Voss, Munich, both of Fed. Rep. of Germany

[73] Assignee: U.S. Philips Corporation, New York, N.Y.

[21] Appl. No.: 29,251

[22] Filed: Mar. 10, 1993

[30] Foreign Application Priority Data

Mar. 10, 1992 [DE] Fed. Rep. of Germany ........ 4207489

[51] Int. Cl.$^5$ ............................................. A61B 5/024
[52] U.S. Cl. .................................. 128/702; 128/706; 601/4
[58] Field of Search ............ 128/24 EL, 28 AA, 702, 128/705, 706, 708

[56] References Cited

U.S. PATENT DOCUMENTS 3,633,569 1/1972 Brayshaw ............................ 128/702
4,745,920 5/1988 Forssmann et al. ............ 128/24 EL
5,181,519 1/1993 Bible .................................... 128/702

FOREIGN PATENT DOCUMENTS 3146628 1/1985 Fed. Rep. of Germany .
90/11052 10/1990 PCT Int'l Appl. .

Primary Examiner—Ruth S. Smith
Attorney, Agent, or Firm—Jack D. Slobod

[57] ABSTRACT

An apparatus for shockwave treatment of a patient, includes a shockwave generator and a detector of a cardiac signal which corresponds to the cardiac action of the patient. During the shockwave treatment, complications to the patient are prevented by the provision of an analyzer for determining extrasystoles in the cardiac signal, a frequency determining circuit which determines the frequency of occurrence of extrasystoles, and a control device responsive to the frequency determining circuit which controls the shockwave generator in dependence on the frequency of occurrence of extrasystoles.

10 Claims, 1 Drawing Sheet

APPARATUS FOR SHOCKWAVE TREATMENT

BACKGROUND OF THE INVENTION

1. Field of the Invention

The invention relates to an apparatus for shockwave treatment, including a shockwave generator and a detector of a cardiac signal corresponding to the cardiac action of the patient.

2. Description of the Related Art

An apparatus of this kind is known from DE-PS 31 46 628. Therein, the cardiac signals are supplied by an ECG probe. They are required to achieve a given, temporal correlation between the ECG signals and the shockwave pulses in order to prevent extrasystoles, i.e. heart beats occurring outside the regular cardiac rhythm. The duration of a shockwave treatment during which a multitude of shockwaves are applied thus depends on the cardiac rhythm of the patient.

SUMMARY OF THE INVENTION

It is an object of the present invention to construct an apparatus of the kind set forth so that circulatory complications are also avoided during a shockwave treatment.

This object is achieved in accordance with the invention by means of
- an analyser for determining extrasystoles in the cardiac signal,
- a circuit for determining the frequency of occurrence of the extrasystoles which is connected subsequent to the analyser, and
- means for controlling the shockwave generator in dependence on the frequency of occurrence of the extrasystoles, which means are controlled by said circuit.

In accordance with the invention, the frequency of the shockwave generation is independent from the cardiac rhythm or from the pulse frequency of the patient. Therefore, it may be higher than in the known apparatus with ECG-synchronous shockwave generation, resulting in shorter treatment times.

In an apparatus in accordance with the invention, extrasystoles can arise when a shockwave pulse lies within the excitable phase of the cardiac action. However, these extrasystoles are detected by the analyser which supplies corresponding signals to a circuit for determining the frequency of occurrence of the extrasystoles. This circuit controls the shockwave generator in dependence on the frequency of occurrence of the extrasystoles so that hazardous situations are effectively precluded.

This can be achieved in different ways. In a particularly simple embodiment of the invention, the means for controlling the shockwave generator deactivate the shockwave generator at least temporarily.

In a further embodiment a further simplification is achieved in that the circuit for determining the frequency of occurrence of the extrasystoles comprises a counter. The counter counts the extrasystoles and induces an (at least temporary) deactivation of the shockwave generator when a given count is reached. In a further embodiment, a timer is provided for resetting the counter after a defined period of time, which timer can be activated by a signal which is supplied by the analyser and which corresponds to an extrasystole. In that case the shockwave generator is influenced only if a given number of extrasystoles occurs within a period of time which is preset by the timer and which is preferably adjustable. Thus, the timer is influenced only if a given temporal density of the extrasystoles occurs; extrasystoles which are spaced far apart in time are less detrimental and can hence be tolerated.

BRIEF DESCRIPTION OF THE DRAWING

The invention will be described in detail hereinafter with reference to the drawing. Therein.

DETAILED DESCRIPTION OF THE PREFERRED EMBODIMENT

Figure 1:
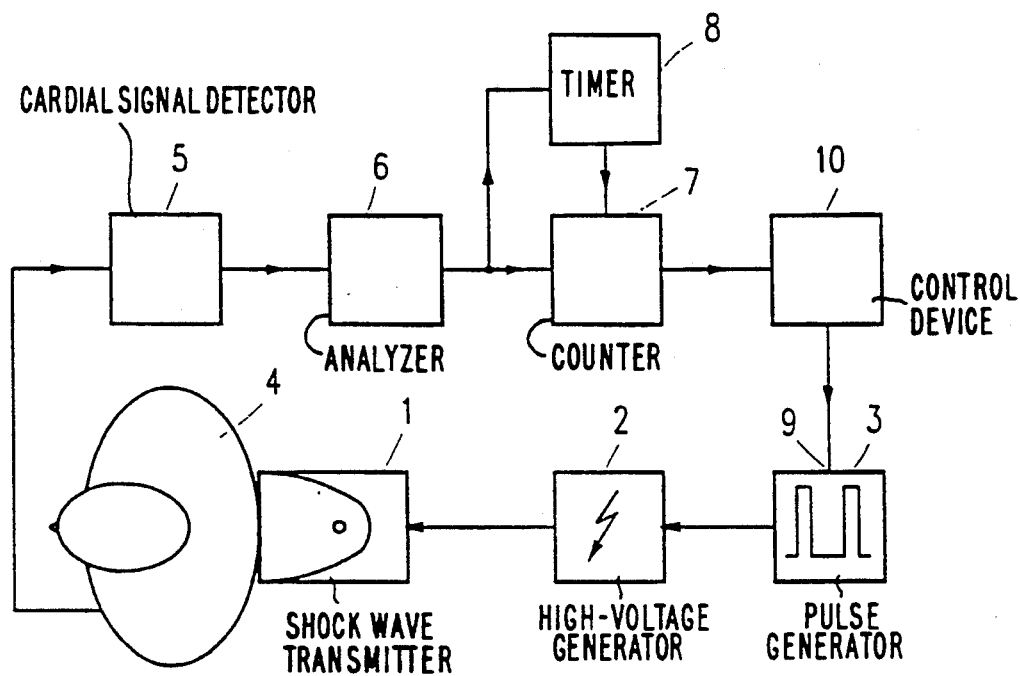
FIG. 1 shows a block diagram of an apparatus in accordance with the invention.

The shockwave generator of the apparatus which is diagrammatically shown in FIG. 1 comprises the units 1, 2 and 3. The unit 1 transmits the actual shockwave. It may comprise an ellipsoid of revolution, in the focal point of which there is provided a spark gap whose ignition causes a pulsed shockwave. The shockwave thus generated is focused onto the second focal point of the ellipsoid of revolution in which there is present a concrement (not shown) of a patient 4, for example a renal calculus to be crushed during a shockwave treatment. However, there may also be provided a shockwave generator which generates the shockwaves in a different manner, for example by means of an electromagnetically driven diaphragm whose shockwaves are focused onto one point by means of reflectors and/or acoustic lenses.

The energy for the unit 1 is delivered by a high-voltage generator 2 which receives a preferably adjustable pulse frequency from a pulse generator 3 and which supplies energy for igniting the spark gap in the unit 1 in response to each pulse.

The patient 4 to be subjected to the shockwave treatment is coupled to a circuit 5 which detects and supplies cardiac signals corresponding to the cardiac action of the patient. Like in said known apparatus, this circuit may be an ECG probe. However, because exact correspondence with the variation in time of the cardiac signals is not required, other circuits capable of supplying such signals can also be used, for example (photoelectric) pulse detectors for circuits which convert the cardiac sounds into electric signals.

The cardiac signals are applied to an analyzer 6 which is capable of detecting extrasystoles and which generates a pulse on its output in response to each extrasystole.

Figure 2:
FIG. 2 shows EGG signals with and without extrasystoles.
Figure 2:

FIG. 2 shows the variation in time of the ECG signals applied to the analyzer, an ECG signal without extrasystoles being shown at the top and an ECG signal containing extrasystoles E being shown at the bottom. The peaks of the signal represent the so-called QRS complex. It appears that in the ECG signal containing extrasystoles E, as shown in the bottom line, the distance in time between the peaks decreases significantly in comparison with a cardiac action without extrasystoles. Therefore, extrasystoles can be comparatively easily detected by measurement of the distance in time between successive peaks. ECG apparatus capable of detecting extrasystoles, are already commercially available, for example the apparatus marketed by the firm Hellige as type SMV 104 D when provided with the relevant module.

The pulses supplied by the analyzer and representing a respective extrasystole E are applied to the input of a circuit 20 which determines the frequency of occurrence of extrasystoles. Circuit 20 contains a resettable counter 7 and a timer 8. The input of circuit 20 is connected on the one hand to the input of the resettable counter 7 and on the other hand to the input of the timer 8, for example a monostable circuit which outputs, after a preferably adjustable time interval, a pulse on its output which is connected to the reset input of the counter, which pulse resets the counter. The output of circuit 20 is formed by the output of counter 7. If a given, preferably presettable count is not reached within the time interval predetermined by the timer 8, the counting of the extrasystoles commences again. In the opposite case, the counter applies a signal to a control device 10 whose output controls a control input 9 of the pulse generator 3 so that the pulse generator 3 is deactivated for a given period of time in response to a signal from the counter 7.

The time interval 8 preset by the timer and the presettable count at which the counter 7 applies a relevant signal to the control unit 10 must be chosen so that the patient can withstand the predetermined number of extrasystoles without complication during the time interval. The period during which the control device 10 deactivates the pulse generator 3, and hence the generation of shockwaves, must be chosen so that the circulation of the patient can regenerate itself during this treatment interval. The values to be adjusted on the units 7, 8 and 10 are preset by the physician on the basis of the constitution of the patient, so that no complications can occur during treatment.

It may be effective to preset, after a first interval, said values so that the pulse generator 3 is deactivated already at a lower frequency of occurence of the extrasystoles or that the second treatment interval becomes longer than the first one. In that case the preset values must be automatically varied during a treatment. This could in principle be achieved by means of an appropriately conceived circuit. However, it is more effective to execute the function of the units 7, 8 and 10 by means of a correspondingly programmed microcomputer which is required any way in a lithotripsy apparatus and which could also take over, if desired, the functions of the units 3 and/or 6.

Instead of interrupting or completely terminating the treatment, it is also possible to reduce the shockwave energy in response to a given frequency of occurrence of the extrasystoles; the control unit 10 should then act on the high-voltage generator 2. With the inclusion of the patient, a control circuit would then be established which can be adjusted so that a given frequency of occurrence of the extrasystoles will not be exceeded.

Should the frequency of occurrence of the extrasystoles still fail to drop below a critical value, the pulse generator could be temporarily or definitely switched off.

What is claimed is:

1. An apparatus for shockwave treatment of a patient, comprising:
    a shockwave generator for generating successive shockwaves in the patient;
    detecting means for detecting a cardiac signal corresponding to cardiac action in the patient;
    an analyzer means, coupled to said detecting means, for detecting occurrences of extrasystoles in the detected cardiac signal;
    frequency determining means fed by said analyzer means for determining a frequency of occurrence of the extrasystoles; and
    control means responsive to said frequency determining means for controlling the shockwave generator in dependence upon the determined frequency of occurrence of the extrasystoles.

2. An apparatus as claimed in claim 1, wherein the frequency determining means comprises a counter means for counting, beginning from an initial state, in response to a signal supplied by the analyzer means which corresponds to an occurrence of an extrasystole.

3. An apparatus as claimed in claim 2, wherein the frequency determining means further comprises timer means, coupled to said counter means and to said analyzer means, for being activated by said signal supplied by said analyzer means and for resetting the counter means to the initial state a predetermined period of time after the timer means is activated.

4. An apparatus as claimed in claim 3, wherein the control means comprises means for inducing a reduction in energy of the shockwaves generated by the shockwave generator.

5. An apparatus as claimed in claim 4, wherein the shockwave generator comprises a generator of successive pulses having an adjustable repetition frequency and means for producing said shockwaves in response to said pulses.

6. An apparatus as claimed in claim 3, wherein the shockwave generator comprises a generator of successive pulses having an adjustable repetition frequency and means for producing said shockwaves in response to said pulses.

7. An apparatus as claimed in claim 2, wherein the shockwave generator comprises a generator of successive pulses having an adjustable repetition frequency and means for producing said shockwaves in response to said pulses.

8. An apparatus as claimed in claim 1, wherein the control means comprises means for deactivating the shockwave generator at least temporarily.

9. An apparatus as claimed in claim 8, wherein the shockwave generator comprises a generator of successive pulses having an adjustable repetition frequency and means for producing said shockwaves in response to said pulses.

10. An apparatus as claimed in claim 1, wherein the shockwave generator comprises a generator of successive pulses having an adjustable repetition frequency and means for producing said shockwaves in response to said pulses.

* * * * *